United States Patent [19]

Ward

[11] Patent Number: 4,643,762
[45] Date of Patent: Feb. 17, 1987

[54] HERBICIDAL 5-AMINO-3-OXO-4-(3-SUBSTITUTED-PHENYL)-4-PYRROLINE AND DERIVATIVES THEREOF

[75] Inventor: Carl E. Ward, San Jose, Calif.

[73] Assignee: Chevron Research Company, San Francisco, Calif.

[21] Appl. No.: 645,452

[22] Filed: Aug. 27, 1984

[51] Int. Cl.$^4$ .................. A01N 43/36; C07D 207/36
[52] U.S. Cl. ........................................ 71/95; 548/541; 71/76
[58] Field of Search ............................ 548/541; 71/95

[56] References Cited

U.S. PATENT DOCUMENTS

| | | | |
|---|---|---|---|
| 3,020,288 | 2/1962 | Wragg et al. | 548/541 |
| 3,510,495 | 5/1970 | Beck | 548/550 |
| 3,577,433 | 5/1971 | Fuks et al. | 548/541 |
| 4,013,445 | 3/1977 | Bellus et al. | 71/95 |
| 4,132,713 | 11/1979 | Broadhurst | 71/95 |

FOREIGN PATENT DOCUMENTS 44-5222  3/1969  Japan .
687070  9/1979  U.S.S.R. .

OTHER PUBLICATIONS

Chem. Abs. 92:41753r.
J. Org. Chem., vol. 41, No. 2 (1976) pp. 390–392.
Tetrahedron v. 23 (1967), pp. 4395–4407.

*Primary Examiner*—Glennon H. Hollrah
*Assistant Examiner*—D. B. Springer
*Attorney, Agent, or Firm*—S. R. LaPaglia; R. C. Gaffney; L. S. Squires

[57] ABSTRACT

5-Amino-3-oxo-4-(substituted-phenyl)-4-pyrroline and derivatives thereof. The compounds generally exhibit both pre-emergence and post-emergence phytotoxicity and are useful as herbicides and also plant growth regulating agents at low dosages.

19 Claims, No Drawings

HERBICIDAL 5-AMINO-3-OXO-4-(3-SUBSTITUTED-PHENYL)-4-PYRROLINE AND DERIVATIVES THEREOF

BACKGROUND OF THE INVENTION

This invention relates to 5-amino-3-oxo-4-(substituted-phenyl)-4-pyrroline derivatives and to the use of such compounds as herbicides and plant growth regulators.

U.S. Pat. No. 3,577,433 is directed to a process for preparing a very broad genus of compounds having the formula:

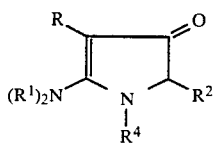

wherein $R^1$ is a hydrocarbon group, such as alkyl, cycloalkyl, aryl, arylalkyl, alkaryl, optionally substituted with groups that are free of reactive hydrogen or $(R^1)_2N$ can form a heterocycle, R is as defined for $R^1$ or is $-NR^1R^1$; and $R^2$ and $R^4$ are independently hydrogen, alkyl, aryl, cyclocalkyl, aralkyl, alkaryl, and the like. The compounds are described as useful as hydrogen halide acceptors and catalysts.

Tetrahedron, Vol. 25, 5721–32 (1969); CA:v 72:43329t discloses 1,4-diphenyl-3-oxo-5-dimethylaminopyrroline as part of an academic discussion. J. Organic Chemistry Vol. 41, pp. 390-2, discloses 1-ethyl-2-(2-carboxyphenyl)-3-oxo-4-phenyl-pyrroline in an academic paper. Based on Chem. Abstracts Vol. 92:41753r, Russian patent document SU No. 687070 discloses 1,4-diphenyl-3-oxo-5-aminopyrroline and the corresponding 2-methyl, ethyl and phenyl derivatives thereof and Chem. Abstracts Vol. 89:163331 describes a paper by Dopov. of the Akad. Nauk. Ukr. RSR, in Ser. B. Geol., Khim. Biol Nauk, Vol. (7), pp. 619–21 as disclosing 1,4-diphenyl-2,2-dimethyl-3-oxo-4-aminopyrroline. Japanese patent document No. 69/5222 (1969)—Chem. Abstracts Vol. 70:115004S discloses 1-methyl-3-oxo-4-phenyl-5-aminopyrroline as a pharmaceutical.

Chemiker-Zeitung 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application No. 13,710/69 (Chemical Abstracts 71:61195e) discloses 5-amino-3-oxo-4-(phenyl or 4-chlorophenyl)-2,3-dihydrofurans. Japanese Pat. No. 19090 (Chemical Abstracts 69P10352e) discloses certain 2,3-dihydrothiophenes as pharmaceuticals. Helvetica Chemica Acta, Volume 66, Pages 362–378 (1983) discloses 5-N-cyclopropyl-4-phenyl-2-methoxycarbonylmethylene-3-furanone as part of an academic chemical synthesis discussion.

In my prior application, Ser. Nos. 505,169; 594,497; and 607,610 filed June 17, 1983, now abandoned; Mar. 29, 1984, now U.S. Pat. No. 4,537,673; and May 9, 1984; now abandoned, respectively, I disclosed certain herbicidally active derivatives of 5-amino-3-oxo-4-substituted phenyl-2,3-dihydrofuran. In my application Ser. No. 623,805, filed June 23, 1984, now U.S. Pat. No. 596,595, I disclosed certain herbicidally active 5-amino-3-oxo-4-substituted phenyl2,3-dihydrothiophene derivatives.

SUMMARY OF THE INVENTION

The present invention provides compounds having both pre-emergence and post-emergence herbicidal activity. The compounds have very good pre-emergence activity against a broad spectrum of both broadleaf weeds and grassy weeds. At lower application rates the compounds also exhibit plant growth regulating properties.

The compounds of the present invention can be represented by the following formula:

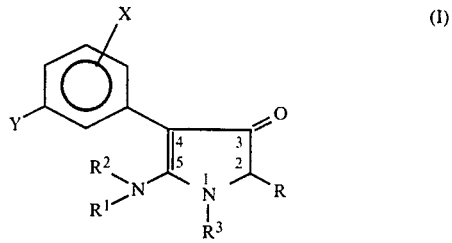

wherein
R is hydrogen, lower alkyl, lower alkenyl, fluoroalkyl having 1 through 4 carbon atoms and 1 through 3 fluoro atoms; fluoroalkenyl having 2 through 4 carbon atoms and 1 through 3 fluoro atoms; phenyl, naphth-1-yl; 4-fluorophenyl; 2,6-difluorophenyl; benzyl; naphth-1-ylmethylene; 2-halobenzyl; 2-lower alkylbenzyl; 3-halobenzyl; 3-lower alkylbenzyl; or substituted phenyl having the formula:

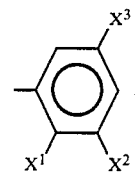

wherein one or two of $X^1$, $X^2$ or $X^3$ is lower alkyl, lower alkoxy, halo, nitro, or haloalkyl having 1 through 3 carbon atoms and 1 through 3 halo atoms independently selected from the group of fluoro, chloro, bromo or iodo; and the other(s) is hydrogen; $R^1$, $R^2$ and $R^3$ are independently hydrogen, methyl or ethyl, with the proviso that if one of $R^1$, $R^2$ or $R^3$ is ethyl, then the other two are each hydrogen;
X is hydrogen, lower alkyl, lower alkoxy, halo, or trifluoromethyl and can be at any available position on the phenyl ring; and
Y is alkyl, having 3 or 4 carbon atoms; alkoxy, having 3 or 4 carbon atoms; alkylthio having 3 or 4 carbon atoms; halo, haloalkoxy having 1 through 3 carbon atoms and 1 through 3 halo atoms; haloalkylthio, having 1 through 3 carbon atoms and 1 through 3 halo atoms; or haloalkyl having 1 through 3 carbon atoms and 1 through 3 halo atoms.

The invention also comprises compatible salts of the compound of Formula (I).

The compounds of Formula (I) exist as keto ⇌ enol isomers and also have an asymmetric carbon atom and can also exist as optical isomers. In some instances the compounds also exist as geometric isomers. The above Formula I is intended to encompass the respective isomers as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 3-6 set forth hereinbelow. In terms of substituents, the preferred compounds are those wherein R is lower alkyl, aryl or substituted aryl, more preferably methyl, phenyl or substituted phenyl, and especially phenyl, monomethylphenyl or monohalophenyl, more preferably, phenyl, 2-methylphenyl, 2-halophenyl, and especially 2-fluorophenyl. Preferably two of $R^1$, $R^2$ and $R^3$ are hydrogen and the other is methyl or hydrogen, ethyl or n-propyl, and more preferably $R^1$ and $R^2$ are hydrogen and $R^3$ is methyl. Preferably, X is hydrogen and Y is trifluoromethyl or halo, especially trifluoromethyl. Also, generally when R is substituted phenyl, it is preferred in terms of herbicidal activity that the substitution is at the ortho or meta position.

The compounds of Formula (I) wherein $R^1$ and $R^2$ are each hydrogen can be prepared via the following schematically represented process:

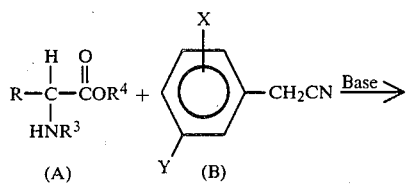

(A)    (B)

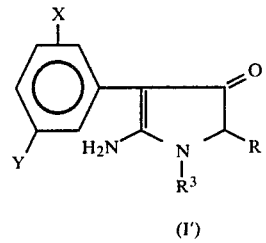

(I')

wherein R, $R^3$ and X and Y are as defined hereinabove; and $R^4$ is lower alkyl, aryl (e.g. phenyl) or arylalkylene (e.g. benzyl).

This process can be conveniently effected by contacting Compound (A) with Compound (B), and a strong base (e.g. sodium methoxide, sodium ethoxide), preferably in an inert organic solvent.

Typically, this process is conducted at temperatures in the range of about from 0° C. to 100° C., preferably 75° C. to 85° C. for about from 5 to 36 hours, preferably 18 to 24 hours, using about from 1.0 to 10.0, preferably 1.0 to 1.2 moles of Compound (A) per mole of Compound (B). Suitable inert organic solvents which can be used include, for example, lower alkanols (e.g. methanol, ethanol, propanol, etc.); tetrahydrofuran; dimethoxyethane; dioxane; and the like, and compatible mixtures thereof.

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formulas (B) are generally known materials and can be prepared by known procedures, or obvious modifications thereof (i.e., substitution of appropriate starting materials). The preparation of Compound (B) is for example described in Org. Syn. Coll., Volume 1, 107 (1941).

The compounds of formula A can be prepared by esterification of the corresponding amino acids. The compounds of Formula (A), wherein R is phenyl or substituted phenyl, can also be prepared via the procedures described in the J. Organic Chemistry, Vol. 29, p. 2764 (1964) or by obvious modifications thereof (e.g. substitution of appropriate reactants and solvents, etc.). Also, more generally, the compounds of Formula A can be prepared via the following schematically represented process:

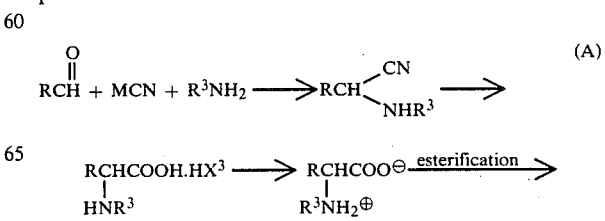

-continued

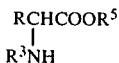

wherein M is a cation, preferably an alkali metal cation; $X^3$ is a mineral acid anion (e.g., chloride), $R^5$ is lower alkyl, and R and $R^3$ are as defined hereinabove.

In the first step of this process an aldehyde having the appropriate R group is contacted with a cyanide salt (preferably in alkali metal cyanide, e.g. potassium cyanide) and a monoamine having the desired $R^3$ group, preferably in an inert organic solvent.

Typically, this reaction is conducted at temperatures in the range of about from 20° C. to 100° C. for about from 1 to 10 hours using about from 1.0 to 5.0 mole equivalents of cyanide salt and 1.0 to 5.0 mole of amine per mole of aldehyde. Suitable solvents which can be used include, for example, aqueous lower alkanol (e.g., ethanol) solutions.

In the next step the previous product is converted to a carboxy acid salt via reaction with a mineral acid, e.g. hydrochloric acid. This process is typically conducted at temperatures in the range of about from 90° C. to 110° C. for about from 24 to 36 hours using at least a mole equivalent amount of mineral acid.

In the next step the acid salt is neutralized via treatment with a base to yield the carboxy ionic intermediate. This can be conveniently effected via treatment with sodium hydroxide. This intermediate can in turn be esterified to compound A using any suitable esterification procedure, such as, for example, via reaction with an alkanol in the presence of an acid catalyst, or as described by A. I. Vogel, "*Practical Organic Chemistry*", 3rd Ed. Page 1000 (1956).

The compounds of Formula A are preferably prepared via the precedure described by W. C. Lo in commonly assigned U.S. application Ser. No. 644,594, filed on even date herewith, and hereby incorporated by reference. This process can be represented by the following overall reaction equation.

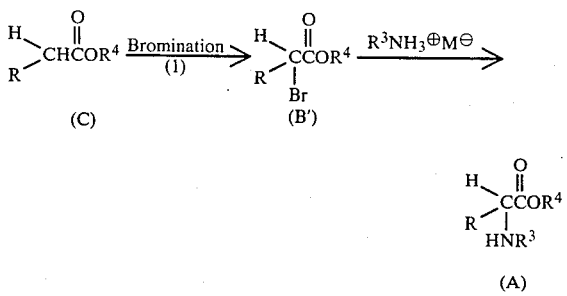

wherein R, $R^3$ and $R^4$ are as defined hereinabove and $M^\ominus$ is an anion, preferably a halide.

This process can be conveniently effected by contacting Compound B' with an ammonium salt having the appropriate $R^3$ group as part of its ammonium cation. Preferably, this process is conducted as a phase transfer reaction in the presence of water, and a water immiscible inert organic solvent and a phase transfer agent. Preferably, the reaction is also conducted in the presence of a weak base, for example, sodium bicarbonate. The weak base serves to liberate low concentrations of methylamine for reaction with the bromoesters (B').

This process is typically conducted at temperatures in the range of about from 0° C. to 100° C., preferably, 40° C. to 45° C., for about from 1 to 60 hours, preferably 18 to 48 hours using about from 1 to 10 moles, preferably 3 to 4 moles of the ammonium salt and 1 to 10 moles, preferably 5 to 6 moles of sodium bicarbonate and 0.05 to 1 moles, preferably 0.05 to 0.1 of benzyltriethylammonium chloride ammonium salt per mole of compound (B').

Suitable inert organic solvents which can be used include, for example, methylene chloride, chloroform, 1,2-dichloroethane, trichloroethane, toluene, and the like.

Suitable phase transfer agents which can be used are reagents and compatible salts thereof which transfer hydrophilic ions into liquid lipophilic organic mediums and include benzyl triethylammonium chloride, methyltrioctylammonium chloride and the like. In place of sodium bicarbonate, the following reagents could be used; potassium bicarbonate, lithium bicarbonate, sodium hydrogen phosphate, potassium hydrogen phosphate and the like.

The compounds of Formula (B') wherein R is hydrogen, lower alkyl, lower alkenyl, fluoroalkyl, fluoroalkenyl, benzyl, naphth-1-ylmethene or substituted benzyl can be conveniently prepared via the general procedure described in "Organic Synthesis", Vol. 4, p. 608 (1963) using the appropriate starting materials and solvents.

The compounds of Formula (B') wherein R is aryl or a substituted aryl can be conveniently prepared via bromination:

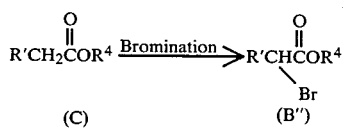

wherein $R^3$ and $R^4$ are as defined hereinabove and R' is aryl or substituted aryl.

The bromination step can be conveniently effected by treating compound (C) with N-bromosuccinimide, in the presence of a suitable catalyst and preferably in an inert organic solvent.

Typically this bromination is conducted at temperatures in the range of about from 0° C. to 100° C., preferably 75° C. to 77° C. for about from 1 to 10 hours, preferably using about 1 to 2 moles, preferably 1 to 1.1 moles, N-bromosuccinimide and about 0 to 1, preferably 0.05 to 0.1 mole of catalyst per mole of compound C. Suitable catalysts which can be used include, for example, dibenzoyl peroxide, di-t-butylperoxide, azobisisobutyronitrile, and the like. Suitable solvents which can be used include, for example, carbon tetrachloride, chlorobenzene, 1,2-dichloroethane, tetrachloroethylene, methylene chloride, and the like and compatible mixtures thereof.

The starting materials of Formula (C) are generally known compounds and can be prepared by known procedures or obvious modifications thereof (e.g., substitution of appropriate starting materials, solvents, etc.). Note, for example, Org. Syn. Coll., Volume 1, p. 270 (1941).

The compound of Formula (I) wherein one or both of $R^1$ and $R^2$ are lower alkyl or lower alkenyl can be prepared by alkylation (or alkenylation) of the amino group:

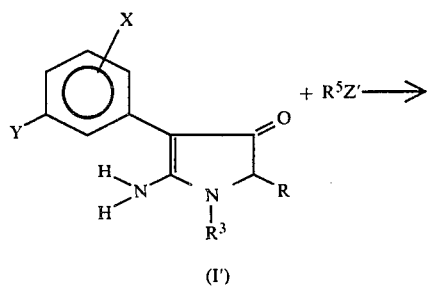

(I')

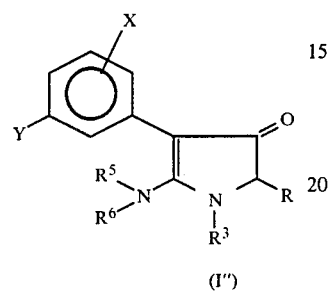

(I'')

wherein R, $R^3$, X and Y are as defined hereinabove; $R^5$ is methyl or ethyl; $R^6$ is hydrogen, methyl or ethyl; and $R^5Z'$ is an alkylation agent.

This process can be effected by contacting Compound (I') with a suitable alkylation agent capable of alkylating primary or secondary amino groups.

For example, this can be effected by contacting Compound (I') with methyl or ethyl iodide, preferably in an inert organic solvent and preferably in the presence of a scavenger base. Typically, this process is conducted at temperatures in the range of about from 0° C. to 100° C., preferably 20° C. to 45° C. for about from 1 to 72, preferably 2.0 to 18.0 hours. Where it is desired to alkylate only one of the external amino hydrogens, then typically about from 1.0 to 1.1 moles of $R^3I$ reactant is used per mole of Compound (I'). Where it is desired to alkylate both amino hydrogens, then typically about from 1.9 to 4 moles of $R^5I$ are used per mole of Compound (I'). Also variation in the amino substituents can be effected by first alkylating only one of the two amino hydrogens and then alkylating the second amino hydrogen with an alkylating agent having a different $R^3$ alkyl or alkenyl group. Suitable inert organic solvents which can be used, include, for example, liquid halogenated alkanes; for example, methylene chloride, carbon tetrachloride, dichloroethane; tetrahydrofuran and the like. Suitable scavenger bases include, for example, the bases described hereinabove with respect to the reaction of Compound (A) with Compound (B).

The compounds of Formula (I'') wherein one of $R^5$ or $R^6$ is methyl or ethyl can be advantageously prepared using dialkyl sulfate as the alkylating agent. This can be conveniently effected by contacting the compound of Formula (I'') with the desired lower alkyl sulfates in the presence of a strong base and preferably in an inert organic solvent in the presence of a phase transfer agent. Typically, this process is conducted at temperatures in the range of about from 0° C. to 100° C., preferably 20° C. to 45° C., using about from 1.0 to 4.0 moles of dialkyl sulfate per mole of Compound (I'). An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures by treating the compound of Formula (I) with a suitable strong base such as, for example, n-butyllithium, sodium hydride, potassium hydride, and the like, having the desired cation, by conventional procedures. Additional variations in the salt cation can also be effected via ion exchange with an ion exchange resin having the desired cation.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 6, preferably 1 through 4, carbon atoms and includes primary, secondary and tertiary alkyl groups. Typical lower alkyls include, for example, methyl, ethyl, n-propyl, isopropyl, n-butyl, t-butyl.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "halo" refers to the group of fluoro, chloro, bromo and iodo.

The term "aryl" refers to aryl groups having 6 through 10 carbon atoms and includes, for example, phenyl, naphthyl, indenyl, and the like.

The term "arylalkylene" refers to the group ArR$^5$- wherein Ar is aryl and R$^5$ is alkylene having 1 through 3 carbon atoms and includes both straight-chained and branched-chained alkylenes, for example, methylene, ethyl, 1-methylethyl, and propyl.

The term "3-oxo-4-pyrroline" refers to the group having the formula:

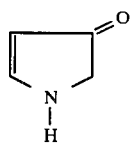

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20° C. to 25° C.

Utility

The compounds of Formula (I) exhibit very good pre-emergence herbicidal activity and to a lesser extent also exhibit post-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05% to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005% to 90% by weight of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade or Celsius system and the term "ambient" or "room temperature" refers to about 20° C. to 25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

EXAMPLE 1

Methyl Bromo-Phenylacetate

This example illustrates the W. Lo process [U.S. application Ser. No. 644,594, filed on even date herewith] for preparing the title compound.

In this example, a mixture containing 5.93 g of N-bromosuccinimide, 5.0 g of methyl phenylacetate; and a catalytic amount (about 0.1 g) of benzoyl peroxide in 0 ml of methylene chloride was warmed to reflux and then refluxed for about four hours. The mixture was then cooled to about 0° C. and filtered. The filtrate was concentrated by evaporation under vacuum affording 7.1 g of the title compound as an oil.

EXAMPLE 2

Methyl Methylamino-phenylacetate

This example illustrates the W. Lo method [U.S. application Ser No. 644,594), filed on even date herewith) for preparing the title compound.

In this example a mixture containing 30.7 g of methyl bromo-phenylacetate, 36.2 g of methyl ammonium chloride (i.e. $CH_3NH_3Cl$); 3.0 g of benzyltriethylammonium chloride and 67.5 g of sodium bicarbonate in about 300 ml of methylene chloride (*and about* 25 ml of water) was warmed to reflux and refluxed for about 18 hours. The mixture was then cooled and washed three times with water, dried over magnesium sulfate and concentrated by vacuum evaporation affording 17.1 g of the title compound as an oil.

Similarly, by following the same procedure but respectively using ethylammonium chloride in place of methylammonium chloride, methyl ethylamino-phenylacetate can be prepared.

Similarly, by following the same procedure but replacing methyl bromo-phenylacetate with methyl 2-bromopropionate; methyl 2-bromo-3-butenate; methyl 2-bromo-3-fluoropropionate; methyl bromo-(3-trifluoromethylphenyl)acetate; methyl bromo-(2-bromophenyl)acetate; methyl bromo-benzylacetate; methyl bromo-(3-nitrophenyl)acetate; and methyl bromo 1-naphthylacetate, the corresponding aminomethylamino and ethylamino esters can also be prepared. (The bromoesters can be prepared by applying the procedure of Example 1 hereinabove or the appropriate procedure described in A. I. Vogel "Practical Organic Chemistry", 3rd Ed., p. 429 (1956) or the procedure described in "Organic Synthesis", Vol. 4, p. 608 (1963) to the appropriate starting materials and in some instances are commercially available.

EXAMPLE 3

1-Methyl-2-phenyl-3-oxo-4-(3-trifluoromethylphenyl)-5-amino-4-pyrroline

In this example, sodium ethoxide was prepared by mixing 3.0 g of metallic sodium with 100 ml of absolute ethanol. After the evolution of hydrogen stopped, a mixture containing 16.0 g of (3-trifluoromethylphenyl)-acetonitrile and 17.1 g of methyl methylamino-phenylacetate was added dropwise to the sodium ethoxide-ethanol mixture. The resulting mixture was then refluxed overnight (about 16 hours) and then cooled to room temperature. The mixture was then added to 300 ml of water and extracted with diethyl ether. The ethyl ether extract was filtered to remove precipitate. The filtrate was concentrated by evaporation affording a solid. This solid was then triturated in ethyl ether. The ethyl ether was then removed from the solid. The solid was washed several times with ethyl ether and then dried overnight affording 6.2 g of the title compound.

Similarly, by applying the above procedure but using the corresponding (substituted phenyl) acetonitrile in place of (3-trifluoromethylphenyl)acetonitrile, the following compounds can be prepared:

1-methyl-2-phenyl-3-oxo-4-(5-chloro-3-trifluoromethylphenyl)-5-amino-4-pyrroline;

1-methyl-2-phenyl-3-oxo-4-(4-chloro-3-trifluoromethylphenyl)-5-amino-4-pyrroline;

1-methyl-2-phenyl-3-oxo-4-(2-bromo-3-trifluoromethylphenyl)-5-amino-4-pyrroline;

1-methyl-2-phenyl-3-oxo-4-(6-fluoro-3-trifluoromethylphenyl)-5-amino-4-pyrroline;

1-methyl-2-phenyl-3-oxo-4-(4-methyl-3-trifluoromethylphenyl)-5-amino-4-pyrroline;

1-methyl-2-phenyl-3-oxo-4-(5-methoxy-3-trifluoromethylphenyl)-5-amino-4-pyrroline;

1-methyl-2-phenyl-3-oxo-4-(6-nitro-3-trifluoromethylphenyl)-5-amino-4-pyrroline;

1-methyl-2-phenyl-3-oxo-4-(3,5-di-trifluoromethylphenyl)-5-amino-4-pyrroline;

1-methyl-2-(3-nitrophenyl)-3-oxo-4-(3-trifluoromethylphenyl)-5-amino-4-pyrroline;

1-methyl-2-benzyl-3-oxo-4-(3-trifluoromethylphenyl)-5-amino-4-pyrroline;

1-methyl-2-(naphth-1-yl)-3-oxo-4-(3-trifluoromethylphenyl)-5-amino-4-pyrroline;

1-methyl-2-(2-bromo-5-nitrophenyl)-3-oxo-4-(3-trifluoromethylphenyl)-5-amino-4-pyrroline;

1-methyl-2-(naphth-1-ylmethylene)-3-oxo-4-(3-trifluoromethylphenyl)-5-amino-4-pyrroline;

1-methyl-2-(2-fluorophenyl)-3-oxo-4-(3-trifluoromethylphenyl)-5-amino-4-pyrroline;

1-methyl-2-phenyl-3-oxo-4-(2-chloro-3-propylphenyl)-5-amino-4-pyrroline;

1-methyl-2-phenyl-3-oxo-4-(4-ethyl-3-butoxyphenyl)-5-5-amino-4-pyrroline;1-methyl-2-phenyl-3-oxo-4-(5-methoxy-3-chlorophenyl)-5-amino-4-pyrroline;

1-methyl-2-phenyl-3-oxo-4-(5-pentyl-3-chlorophenyl)-5-amino-4-pyrroline;

1-methyl-2-phenyl-3-oxo-4-(3,5-dipropoxyphenyl)-5-amino-4-pyrroline;

1-methyl-2-(3-nitrophenyl)-3-oxo-4-(3-bromophenyl)-5amino-4-pyrroline;

1-methyl-2-benzyl-3-oxo-3-(2-chloro-3-fluorophenyl)-5amino-4-pyrroline;

1-methyl-2-(naphth-1-yl)-3-oxo-4-(3-bromo-2-ethylphenyl)-5-amino-4-pyrroline;

1-methyl-2-(naphth-1-yl)-3-oxo-4-(3,4-dibutylphenyl)-5-amino-4-pyrroline;

1-methyl-2-(naphth-1-ylmethylene)-3-oxo-4-(2,3-difluorophenyl)-5-amino-4-pyrroline;

1-methyl-2-(3-fluorobenzyl)-3-oxo-4-(3-iodo-4-methylphenyl)-5-amino-4-pyrroline;

1-methyl-2-phenyl-3-oxo-4-(3-chlorophenyl)-5-amino-4pyrroline;

1-methyl-2-phenyl-3-oxo-4-(3-propylphenyl)-5-amino-4pyrroline;

1-methyl-2-phenyl-3-oxo-4-[3-(2,2-dichloroethylthio)-phenyl]-5-amino-4-pyrroline;

1-methyl-2-phenyl-3-oxo-4-(3-trifluoromethoxyphenyl)-5-amino-4-pyrroline;

1-methyl-2-phenyl-3-oxo-4-(3-bromophenyl)-5-amino-4pyrroline;

-methyl-2-phenyl-3-oxo-4-(3-iodophenyl)-5-amino-4pyrroline;
1-methyl-2-phenyl-3-oxo-4-(3-fluoromethylthiophenyl)-amino-4-pyrroline;
1-methyl-2-phenyl-3-oxo-4-[3-(2,3,3-trifluoropropoxy)phenyl]-5-amino-4-pyrroline;
1-methyl-2-phenyl-3-oxo-4-(3-fluorophenyl)-5-amino-4yrroline; and
1-methyl-2-methyl-3-oxo-4-(3-isopropyl)-5amino-4-pyrroline.

Similarly, by respectively using methyl ethylaminophenylacetate and amino-phenylacetate in place of methyl methylamino-phenylacetate, the corresponding 1-ethyl homologs and 1-desmethyl homologs of the above compounds can be made, for example, 1-ethyl-2-phenyl-3-oxo-4-(3-trifluoromethylphenyl)-5-amino-4-pyrroline and 2-phenyl-3-oxo-4-(3-trifluoromethylphenyl)5-amino-4-pyrroline.

EXAMPLE 4

1-methyl-2-phenyl-3-oxo-4-(-3-trifluoromethylphenyl)-5-methylamino-4-pyrroline

In this example, 4.1 g of 1-methyl-2-phenyl-3-oxo-4-(3-trifluoromethylphenyl)-5-amino-4-pyrroline, was added to 100 ml of methylene chloride containing 1.0 g of sodium hydroxide, dissolved in 4.0 ml of water, and 0.28 g of benzyltriethylammonium chloride at room temperature. Dimethyl sulfate (1.17 ml) dissolved in 20 ml of methylene chloride was admixed dropwise to the aforementioned mixture at room temperature. After the addition was complete, another 0.28 g of benzyltriethylammonium was added and the mixture was stirred at room temperature for 18 hours. At the end of this time, a white precipitate was collected from the mixture by filtration. This solid was stirred with 50 ml of 1N aqueous hydrochloric acid for two hours after which it was collected with suction filtration and washed with aqueous sodium bicarbonate solution followed by water. The solid was dried affording 1.0 g of the title compound as a white powder.

Similarly, by applying the same procedure using the corresponding 5-amino derivatives as starting materials (which in turn can be prepared by applying the procedures of Examples 1–3 hereinabove using the appropriate starting materials), the corresponding 5-methylamino homologs thereof can be prepared, for example:
2-phenyl-3-oxo-4-(5-chloro-3-trifluoromethylphenyl)-5-methylamino-4-pyrroline;
2-phenyl-3-oxo-4-(4-chloro-3-trifluoromethylphenyl)-5-methylamino-4-pyrroline;
2-phenyl-3-oxo-4-(2-bromo-3-trifluoromethylphenyl)-5-5-methylamino-4-pyrroline;
2-phenyl-3-oxo-4-(6-fluoro--3-trifluoromethylphenyl)-5-methylamino-4-pyrroline;
2-phenyl-3-oxo-4-(4-methyl-3-trifluoromethylphenyl)-5-methylamino-4-pyrroline;
2-phenyl-3-oxo-4-(5-methoxy-3-trifluoromethylphenyl)-5-methylamino-4-pyrroline;
2-phenyl-3-oxo-4-(6-propyl-3-trifluoromethylphenyl)-5-methylamino-4-pyrroline;
2-phenyl-3-oxo-4-(3,5-di-trifluoromethylphenyl)-5-methylamino-4-pyrroline;
2-(3-nitrophenyl)-3-oxo-4-(3-trifluoromethylphenyl)-5-methylamino-4-pyrroline;
2-benzyl-3-oxo-4-(3-trifluoromethylphenyl)-5-methylamino-4-pyrroline;
2-(naphth-1-yl)-3-oxo-4-(3-trifluoromethylphenyl)-5-methylamino-4-pyrroline;
2-(2-bromo-5-nitrophenyl)-3-oxo-4-(3-trifluoromethylphenyl)-5-methylamino-4-pyrroline;
2-(naphth-1-ylmethylene)-3-oxo-4-(3-trifluoromethylphenyl)-5-methylamino-4-pyrroline;
2-(2-fluorophenyl)-3-oxo-4-(3-trifluoromethylphenyl)-5-methylamino-4-pyrroline; and
2-phenyl-3-oxo-4-(2-chloro-3-propylphenyl)-5-methylamino-4-pyrroline;
2-phenyl-3-oxo-4-(4-ethyl-3-butoxyphenyl)-5-methylamino-4-pyrroline;
2-phenyl-3-oxo-4-(5-methoxy-3-chlorophenyl)-5-methylamino-4-pyrroline;
2-phenyl-3-oxo-4-(5-hexyl-3-chlorophenyl)-5-methylamino-4-pyrroline;
2-phenyl-3-oxo-4-(3,5-dipropoxyphenyl)-5-methylamino-4-pyrroline;
2-(3-nitrophenyl)-3-oxo-4-(3-bromophenyl)-5-methylamino-4-pyrroline;
2-benzyl-3-oxo-4-(2-chloro-3-fluorophenyl)-5-methylamino-4-pyrroline;
2-(naphth-1-yl)-3-oxo-4-(3-bromo-2-ethylphenyl)-5-methylamino-4-pyrroline;
2-(fluoromethyl)-3-oxo-4-(3,4-dibutylphenyl)-5-methylamino-4-pyrroline;
2-(2-naphth-1-ylmethylene)-3-oxo-4-(2,3-difluorophenyl)-5-methylamino-4-pyrroline;
2-(3-fluorobenzyl)-3-oxo-4-(3-iodo-4-methylphenyl)-5-methylamino-4-pyrroline;
2-phenyl-3-oxo-4-(3-chlorophenyl)-5-methylamino-4-pyrroline;
2-phenyl-3-oxo-4-(3-propylphenyl)-5-methylaminopyrroline;
2-phenyl-3-oxo-4-[3(2,2-dichloroethylthio)phenyl]-5-methylamino-pyrroline;
2-phenyl-3-oxo-4-(3-trifluoromethoxy)-5-methylaminopyrroline;
2-phenyl-3-oxo-4-(3-bromophenyl)-5-methylaminopyrroline;
2-phenyl-3-oxo-4-(3-iodophenyl)-5-methylaminopyrroline;
2-phenyl-3-oxo-4-(3-fluoromethylthiophenyl)-5-methylamino-pyrroline;
2-(2-phenyl)-3-oxo-4-[3-(2,3,3-trifluoropropoxy)phenyl]-5-methylamino-pyrroline;
2-phenyl-3-oxo-4-(3-fluorophenyl)-5-methylaminopyrroline;
2-phenyl-3-oxo-4-(3-isopropylphenyl)-5-methylaminopyrroline;
1-methyl-2-methyl-3-oxo-4-(3-trifluoromethylphenyl)-5-methylamino-4-pyrroline;
1-ethyl-2-phenyl-3-oxo-4-(3-trifluoromethylphenyl)-5-methylamino-4-pyrroline;
1,2-dimethyl-3-oxo-4-(3-trifluoromethylphenyl)-5-methylamino-4-pyrroline;
1-ethyl-2-fluoromethyl-3-oxo-4-(3-bromophenyl)-5-amino-4-pyrroline;
1-methyl-2-(3-trifluoromethylphenyl)-3-oxo-4-(5-chloro-3-trifluoromethylphenyl)-3-oxo-5-methylamino-4-pyrroline;
2-(2-bromophenyl)-3-oxo-4-(3-butylphenyl)-5-methylamino-4-pyrroline;
1-ethyl-2-benzyl-3-oxo-4-(3-butoxyphenyl)-5-amino-4-pyrroline;

1-methyl-2-(3-t-butyl)-3-oxo-4-(2-chloro-3-methylphenyl)-5-methylamino-4-pyrroline; and
2-(naphth-1-yl)-3-oxo-4-(3-trifluoromethylphenyl)-5-methylamino-4-pyrroline.

Similarly, by approximately doubling the amount of dimethylsulfate and increasing the reaction time and/or temperature, the corresponding 5-dimethylamino homologs thereof can be prepared.

EXAMPLE 5

Lithium salt of 2-phenyl-3-oxo-4-(3-trifluoromethylphenyl)-5-amino-4-pyrroline

The lithium salts of the present invention can be prepared by the following procedure.

5.6 ml of 1.6 M n-butyllithium in hexane is added dropwise to a stirred solution containing 2.86 g of 2-phenyl-3-oxo-4-(3-trifluoromethylphenyl)-5-amino-4-pyrroline in 25 ml of tetrahydrofuran at -30° C. The resulting mixture is stirred for 20 minutes and then concentrated in vacuo to afford the title compound.

Similarly, by following the same procedure, the corresponding lithium salts of the compounds of Examples 2-5 can also be prepared.

EXAMPLE 6

The compounds listed in Table A hereinbelow were prepared using the appropriate starting materials and procedures described in the Examples hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/L.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots

TABLE A

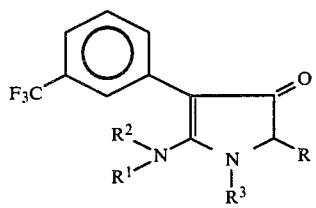

| No. | R$^1$ | R$^2$ | R$^3$ | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|---|
| 1 | H | H | H | φ** | 64.15 | 64.21 | 4.09 | 4.3 | 8.81 | 8.58 | 104–109 |
| 2 | H | H | —CH$_3$ | φ | 65.06 | 64.41 | 4.52 | 4.73 | 8.43 | 8.55 | 207–209* |
| 3 | H | —CH$_3$ | —CH$_3$ | φ | 65.90 | 66.03 | 4.91 | 4.98 | 8.09 | 8.19 | 221–223* |
| 4 | H | H | —CH$_2$CH$_3$ | φ | 65.90 | 65.82 | 4.91 | 5.04 | 8.09 | 8.04 | 207–210* |
| 5 | H | H | —CH$_3$ | 2-Clφ | 58.94 | 57.11 | 3.82 | 4.21 | 7.64 | 7.99 | 199–201* |
| 6 | H | H | —CH$_3$ | 3-Clφ | 58.94 | 59.48 | 3.82 | 4.15 | 7.64 | 7.71 | 207–209* |
| 7 | H | H | —CH$_3$ | 4-Clφ | 58.94 | 60.52 | 3.82 | 4.36 | 7.64 | 7.77 | 212–213* |
| 8 | H | —CH$_3$ | —CH$_3$ | 2-Clφ | 59.93 | 59.05 | 4.21 | 4.08 | 7.36 | 7.22 | 241–242* |
| 9 | H | H | —CH$_3$ | 2-Fφ | 61.71 | 60.56 | 4.00 | 4.36 | 8.00 | 8.06 | 213–214* |
| 10 | H | —CH$_3$ | —CH$_3$ | 2-Fφ | 62.64 | 61.64 | 4.4 | 4.38 | 7.69 | 7.58 | 226–229* |
| C-1 | H | —CH$_3$ | —CH$_2$CH$_3$ | φ | 66.67 | 68.46 | 5.28 | 5.5 | 7.78 | 8.19 | 188–192* |

* = Decomposition
φ** = Phenyl, for example, 2-Clφ = 2-chlorophenyl
C-1 = Comparison Compound:
1-ethyl-2-phenyl-3-oxo-4-(3-trifluoromethylphenyl)-5-methylamino-4-pyrrolidone

EXAMPLE 7

In this example, the compounds of Table A were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

containing plants 2 to 3 inches tall (except wild oats, soybean and watergrass which were 3 to 4 inches tall) (approximately 15 to 25 plants per pot) at a dose of 27.5 microgram/cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 80 | 100 | 100 | 65 | 100 | 60 | 60 | 40 |
| 2 | 98 | 98 | 98 | 70 | 100 | 100 | 100 | 70 |
| 3 | 100 | 100 | 100 | 40 | 90 | 90 | 80 | 30 |
| 4 | 50 | 0 | 75 | 0 | 0 | 30 | 0 | 0 |
| 5 | 100 | 100 | 100 | 95 | 100 | 100 | 100 | 98 |
| 6 | 100 | 95 | 100 | 30 | 98 | 98 | 98 | 70 |
| 7 | 0 | 0 | 0 | 0 | 0 | 0 | 0 | 0 |
| 8 | 20 | 30 | 50 | 0 | 0 | 0 | 0 | 0 |
| 9 | 100 | 100 | 100 | 100 | 100 | 100 | 100 | 100 |
| 10 | 100 | 100 | 100 | 80 | 95 | 95 | 60 | 20 |
| C-1 | 0 | 0 | 0 | 0 | 0 | 0 | 0 | 0 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 0 | 33 | 0 | 0 | 0 | 0 | 0 | 0 |
| 2 | 30 | 30 | 50 | 50 | 30 | 0 | 0 | 0 |
| 3 | 30 | 40 | 30 | 30 | 0 | 0 | 0 | 0 |
| 4 | 0 | 0 | 0 | 0 | 0 | 0 | 0 | 0 |
| 5 | 0 | 0 | 0 | 0 | 0 | 0 | 0 | 0 |
| 6 | 0 | 0 | 0 | 0 | 0 | 0 | 0 | 0 |
| 7 | 30 | 30 | 30 | 50 | 0 | 0 | 0 | 0 |
| 8 | 40 | 30 | 40 | 60 | 0 | 0 | 0 | 0 |
| 9 | 20 | 30 | 20 | 30 | 0 | 0 | 0 | 0 |
| 10 | 30 | 50 | 50 | 50 | 20 | 20 | 0 | 0 |
| C-1 | 0 | 0 | 0 | 0 | 0 | 0 | 0 | 0 |

As can be seen from the above Table 1, the compounds of the invention generally exhibit a broad spectrum of excellent pre-emergence phytotoxic activity and especially so Compounds Nos. 2, 5, 6, 9, and 10. Also, as shown by Table 2 a number of the compounds also exhibit modest post-emergence phytotoxic activity against broadleaf plants. Compound No. 7 failed to exhibit preemergence activity in this test but exhibited modest post-emergence phytotoxicity against broadleaf plants. Also, it can be seen that Comparison Compound C-1 was wholly inactive in this test even though it is a methyl homolog of the Compound No. 3, of the present invention, which exhibited very good pre-emergence herbicidal activity.

Obviously, many modifications and variations of the invention described hereinabove and below can be made without departing from the essence and scope thereof.

What is claimed is:

1. A compound having the formula:

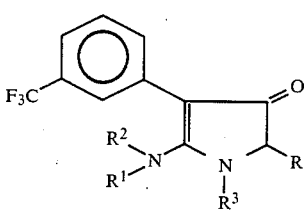

(I)

wherein

R is phenyl or monosubstituted phenyl having the formula:

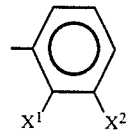

wherein one of $X^1$ or $X^2$ is lower alkyl, lower alkoxy, halo, nitro, or haloalkyl having 1 through 3 carbon atoms and 1 through 3 halo atoms independently selected from the group of fluoro, chloro, bromo or iodo; and the other is hydrogen; and $R^1$, $R^2$ and $R^3$ are independently hydrogen, methyl, or ethyl with the proviso that if one of $R^1$, $R^2$ or $R^3$ is ethyl, then the other two are each hydrogen;

and compatible salts thereof.

2. The compound of claim 1 wherein $R^1$, $R^2$ and $R^3$ are independently hydrogen or methyl.

3. The compound of claim 2 wherein one of $R^1$ or $R^2$ is hydrogen.

4. The compound of claim 3 wherein R is phenyl or halophenyl or trifluoromethylphenyl or alkylphenyl.

5. The compound of claim 4 wherein R is phenyl, 2-halophenyl, or 2-methylphenyl.

6. The compound of claim 3 wherein R is phenyl, 2-halophenyl or 2-lower alkylphenyl.

7. The compound of claim 6 wherein $R^1$, $R^2$ and $R^3$ are hydrogen.

8. The compound of claim 3 wherein R is phenyl, monofluorophenyl, monochlorophenyl, or monomethylphenyl.

9. The compound of claim 8 wherein R is phenyl and $R^1$, $R^2$ and $R^3$ are hydrogen.

10. The compound of claim 3 wherein two of $R^1$, $R^2$ and $R^3$ are hydrogen and the other is hydrogen or methyl.

11. The compound of claim 10 wherein R is monofluorophenyl.

12. The compound of claim 10 wherein R is phenyl.

13. The compound of claim 10 wherein R is 2-fluorophenyl.

14. The compound of claim 13 wherein $R^2$ and $R^3$ are each hydrogen.

15. The compound of claim 13 wherein $R^1$ is hydrogen.

16. A herbicidal composition comprising a herbicidally effective amount of the compound of claim 1, or mixtures of such compounds, and a compatible carrier.

17. A herbicidal composition comprising a pre-emergent herbicidally effective amount of the compound of claim 1, or mixtures thereof, and a compatible carrier.

18. A method for destroying plants which comprises applying a herbicidally effective amount of the compound of claim 1, or mixtures thereof, to the foliage or growth medium of said plants or their seeds.

19. A method for destroying plants which comprises applying a pre-emergent herbicidally effective amount of the compound of claim 1, or mixtures thereof, to the growth medium of said plants or their seeds.

* * * * *